United States Patent [19]

Gauthier et al.

[11] 4,379,926

[45] Apr. 12, 1983

[54] 1,4,5,6-TETRAHYDROPYRIMIDINE DERIVATIVES

[75] Inventors: Jean A. Gauthier; Ivo Jirkovsky, both of Montreal, Canada

[73] Assignee: Ayerst, McKenna & Harrison Ltd., Montreal, Canada

[21] Appl. No.: 904,124

[22] Filed: May 8, 1978

[51] Int. Cl.$^3$ ............... C07D 413/06; C07D 239/06; A61K 31/505; A61K 31/535

[52] U.S. Cl. ........................... 544/122; 424/251; 424/248.4; 542/458; 544/242; 544/330; 544/332; 544/333; 544/335

[58] Field of Search ............ 549/242, 330, 333, 335, 549/332, 122; 542/458

[56] References Cited

U.S. PATENT DOCUMENTS

| | | | |
|---|---|---|---|
| 2,658,895 | 11/1953 | Ballard et al. | 544/242 |
| 3,126,381 | 3/1964 | Langis et al. | 544/242 |
| 3,332,948 | 7/1967 | Blatter | 544/335 |
| 3,814,758 | 6/1974 | Kessler et al. | 544/333 |
| 3,926,994 | 12/1975 | White et al. | 424/256 |
| 4,003,718 | 1/1977 | Gattuso et al. | 544/122 |
| 4,007,200 | 2/1977 | Panzer et al. | 544/335 |

OTHER PUBLICATIONS

Skinner et al., "J. Amer. Chem. Soc.", vol. 73, 1951, pp. 3814.

Faust et al., "J. Org. Chem.", vol. 26, 1961, pp. 4044.

Primary Examiner—Donald G. Daus
Assistant Examiner—James H. Turnipseed
Attorney, Agent, or Firm—Arthur E. Wilfond

[57] ABSTRACT 1,4,5,6-Tetrahydropyrimidine derivatives characterized by having a phenyl or substituted phenyl at positions 1 and 6 in addition being further substituted at position 2. The foregoing compounds are useful as diuretic agents in a mammal. Methods for the preparation and use of the compounds are disclosed.

12 Claims, No Drawings

1,4,5,6-TETRAHYDROPYRIMIDINE DERIVATIVES

BACKGROUND OF THE INVENTION (a) Field of the Invention

This invention relates to novel 1,4,5,6-tetrahydropyrimidine derivatives, to therapeutically acceptable salts thereof, to processes for their preparation, to methods for using the derivatives and to compositions of the derivatives.

More specifically, the present invention relates to novel 1,4,5,6-tetrahydropyrimidine derivatives having a phenyl or substituted phenyl at positions 1 and 6 and in addition being further substituted at position 2. These derivatives are useful as diuretic and saluretic agents without appreciably affecting potassium excretion in a mammal at dosages which do not elicit undesirable side effects.

(b) Description of the Prior Art

A rather large number of reports dealing with 1,4,5,6-tetrahydropyrimidine derivatives are available. More specifically, a number of phenyl substituted 1,4,5,6-tetrahydropyrimidine derivatives have been reported. For example, the report of G. S. Skinner and P. R. Wunz, J. Amer. Chem. Soc., 73, 3814 (1951) discloses 2-phenyl, 2-benzyl and 2-phenylethyl derivatives having pressor activity and the report of J. A. Faust et al., J. Org. Chem., 26, 4044 (1961) discloses 2-(halobenzyl) derivatives having pressor, adrenolytic and sympatholytic activities. Still other examples are the following reports disclosing other phenyl substituted 1,4,5,6-tetrahydropyrimidine derivatives: H. M. Blatter, U.S. Pat. No. 3,332,948, issued July 25, 1967 disclosing 1-(substituted phenyl) derivatives having diuretic and natriuretic activities, and A. C. White and R. M. Black, U.S. Pat. No. 3,926,994, issued Dec. 16, 1975 disclosing 2-benzyl or 2-(substituted benzyl) derivatives having hypoglycaemic, diuretic, antiinflammatory and cardiovascular activities.

The compounds of the present invention are structurally different from the prior art compounds by having a phenyl or substituted phenyl at positions 1 and 6 on the 1,4,5,6-tetrahydropyrimidine ring as well as being substituted at position 2. In addition, the compounds of this invention are prepared using phosphorus oxychloride, a dehydrating agent previously not employed for the preparation of 1,4,5,6-tetrahydropyrimidines,

SUMMARY OF THE INVENTION

The compounds of this invention are represented by formula I

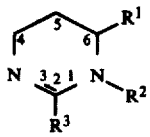

in which $R^1$ and $R^2$ each is phenyl or phenyl monosubstituted with lower alkyl, halo or lower alkoxy; and $R^3$ is lower alkyl; lower cycloalkyl; phenyl; phenyl mono- or disubstituted with lower alkyl, halo, trifluoromethyl or lower alkoxy; 2- or 3-furyl; 2-, 3- or 4-pyridinyl; 2- or 3-thienyl; lower alkylamino; di(lower alkyl)amino; or a radical of formula $R^4$—A wherein A is lower alkylene or lower alkenylene and $R^4$ is chloro; bromo; phenyl; phenyl mono- or disubstituted with lower alkyl, halo, trifluoromethyl or lower alkoxy; lower alkylamino; di(lower alkyl)amino; 1-piperidinyl or 4-morpholinyl.

A preferred group of compounds of this invention are represented by formula I in which $R^1$ and $R^2$ are phenyl; and $R^3$ is lower alkyl; phenyl; phenyl mono- or disubstituted with lower alkoxy; 2- or 3-furyl; 2-, 3- or 4-pyridinyl; 2- or 3-thienyl; di(lower alkyl)amino; or a radical of formula $R^4$—A wherein A is lower alkylene or lower alkenylene and $R^4$ is phenyl, 3,4-dimethoxyphenyl, di(lower alkyl)amino, 1-piperidinyl or 4-morpholinyl.

Another preferred group of compounds of this invention is represented by formula I in which $R^1$ and $R^2$ are phenyl and $R^3$ is lower alkyl, phenyl, 2-furyl, 3-pyridinyl, 2-thienyl, di(lower alkyl)amino or a radical of formula $R^4$—A wherein A is lower alkylene and $R^4$ is 1-piperidinyl or 4-morpholinyl.

Another preferred group of compounds of this invention is represented by formula I in which $R^1$ and $R^2$ are phenyl and $R^3$ is lower alkyl, phenyl or di(lower alkyl)amino.

Another preferred group of compounds of this invention is represented by formula I in which $R^1$ and $R^2$ are phenyl and $R^3$ is 2-furyl, 3-pyridinyl, 2-thienyl or a radical of formula $R^4$—A wherein A is lower alkylene and $R^4$ is 1-piperidinyl or 4-morpholinyl.

The compounds of formula I in which $R^1$, $R^2$ and $R^3$ are as defined herein are prepared by a process, which comprises cyclizing a compound of formula II

$$R^2\text{—NH—CH}(R^1)\text{CH}_2\text{CH}_2\text{—NH—COR}^3 \qquad \text{(II)}$$

in which $R^1$, $R^2$ and $R^3$ are as defined herein in the process of phosphorus oxychloride, and when desired, reacting the compound of formula I with a therapeutically acceptable acid to obtain the corresponding therapeutically acceptable acid addition salt of the compound of formula I in which $R^1$, $R^2$ and $R^3$ are as defined herein.

The therapeutically acceptable acid addition salts of the compounds of formula I are included within the scope of this invention.

The compounds of this invention increase the excretion of urine (diuresis) in a mammal, by administering to the mammal an effective diuretic amount of a compound of formula I or a therapeutically acceptable acid addition salt thereof.

The compounds of this invention increase the antagonizing renal mineralocorticoid action in a mammal, by administering to the mammal an effective renal mineralocorticoid antagonizing amount of the compound of formula I, or a therapeutically acceptable acid addition salt thereof.

The compounds of this invention increase the excretion of urine in a mammal without excessive loss of potassium, by administering to the mammal an effective renal mineralocorticoid antagonizing amount of the compound of formula I or a therapeutically acceptable acid addition salt thereof, in combination with an effective amount of a non-mineralocorticoid antagonizing diuretic agent.

The compounds of this invention reverse or prevent secondary aldosteronism and potassium depletion induced in a mammal undergoing diuretic therapy, by administering to the mammal an effective renal mineralocorticoid antagonizing amount of the compound of formula I, or a therapeutically acceptable acid addition salt thereof, to significantly reverse or prevent the secondary aldosteronism and potassium depletion caused by the diuretic agent alone.

Another aspect of this invention involves a pharmaceutical composition comprising a compound of formula I, or a therapeutically acceptable salt thereof, and a pharmaceutically acceptable carrier.

Still another aspect of this invention involves a pharmaceutical composition comprising a compound of formula I, or a therapeutically acceptable acid addition salt thereof, in combination with a non-mineralocorticoid antagonizing diuretic agent and a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexyloxy and the like.

The term "lower alkylene" as used herein means a divalent organic radical derived from either straight and a branched chain aliphatic hydrocarbons containing from one to six carbon atoms by removal of two hydrogen atoms and includes methylene, ethylene, 1-methylpropylene, 2-ethylpropylene, 2-butylethylene and the like.

The term "(lower)alkylene" as used herein means a divalent organic radical derived from either straight and branched chain alkene hydrocarbons containing from two to six carbon atoms by removal of two hydrogen atoms and includes ethenylene, 1-propenylene, 2-methyl-2-propenylene, 2-butenylene and the like.

The term "lower cycloalkyl" as used herein means saturated cyclic hydrocarbon radicals containing from three to six carbon atoms and includes cyclopropyl, cyclobutyl, cyclopentyl and cyclohexyl.

The term "halo" as used herein means halogens and includes fluorine, chlorine, bromine and iodine, unless stated otherwise.

The term "lower alkanol" as used herein means both straight and branched chain alkanols containing from one to four carbon atoms and includes methanol, ethanol, isopropanol, butanol and the like.

The term "organic proton acceptor" as used herein means the organic bases, or amines for instance, triethylamine, pyridine, N-ethylmorpholine, 1,5-diazabicyclo[3.4.0]nonene-5 and the like.

The term "inorganic proton acceptor" as used herein means the inorganic bases, preferably the alkali metal hydroxides, carbonates, hydrides, amides and alkoxides, for example, sodium ethoxide, sodium methoxide, sodium hydride and the like.

The symbol $C_6H_5$ represents phenyl.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl or an ethanol-diethyl ether mixture. These salts, when administered to a mammal, possess the same pharmacologic activities as the corresponding bases. For many purposes it is preferable to administer the salts rather than the base compounds. Suitable acids to form these salts include the common mineral acids, for instance hydrohalic, sulfuric or phosphoric acid; as well as the organic acids, for instance, formic, acetic, maleic, citric, or tartaric acid; or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers, contained therein. It is to be understood that the diastereomers arising from such asymmetry are included within the scope of this invention. Such diastereomers are obtained in substantially pure form by classical separation techniques and by sterically controlled synthesis.

Individual optical enantiomers, which might be separated by fractional crystallization of the diastereomeric salts thereof, for instance, salts with d- or l-tartaric acid or D-(+)-α-bromocamphor sulfonic acid, are also included.

The compounds of this invention of formula I, or a therapeutically acceptable acid addition salt thereof, are useful diuretic agents in a mammal upon oral or parenteral administration.

The compounds of formula I have been shown to be effective diuretic agents in mammals by tests conducted in dogs or rats. An example of such a test for diuretic agents in rats is described by J. R. Cummings et al., J. Pharmacol. Exp. Ther., 414, 128 (1960). In this test, the urine of the rats is collected for five hours, during which time food and water are withdrawn. Urine volumes as well as sodium, potassium and chloride ion concentrations are determined. The compounds of this invention exhibit a dose response dependency when they are orally administered in dosages ranging from 5 to 200 mg per kilogram of body weight. The following representative compounds of formula I were subjected to the above-described test and shown to be effective diuretic agents when administered orally to the rat (the effective oral dose in mg per kilogram of body weight is indicated in the parentheses): 1,2,6-triphenyl-1,4,5,6-tetrahydropyrimidine (6.25 mg, described in Example 9), 2-(1,1-dimethylethyl)-1,6-diphenyl-1,4,5,6-tetrahydropyrimidine (25 mg, described in Example 61), 2-methyl-1,6-diphenyl-1,4,5,6-tetrahydropyrimidine (25 mg, described in Example 62), 1,6-diphenyl-2-(3,4-dimethoxyphenyl)-1,4,5,6-tetrahydropyrimidine (50 mg, described in Example 63), 2-dimethylamino-1,6-diphenyl-1,4,5,6-tetrahydropyrimidine (50 mg, described in Example 67) and 1,6-diphenyl-2-(3-pyridinyl)-1,4,5,6-tetrahydropyrimidine (100 mg, described in Example 77).

In addition to having the diuretic activity as exemplefied in the above test, the compounds of formula I antagonize the renal actions of mineralocorticoids and thus are diuretic agents which cause an increase in urine volume as well as sodium and chloride excretion without affecting potassium excretion.

Aldosterone is a naturally occuring mineralocorticoid of the adrenal cortex which promotes the reabsorption of sodium and chloride and the excretion of potassium, hydrogen and ammonium ions in the distal renal tubules. Hyperaldosteronism is found in a number of pathological conditions. Hyperaldosteronism can be corrected by the administration of a diuretic agent which antagonize the renal action of aldosterone.

Antialdosterone activity can be demonstrated in standard test systems. One such test is described by C. M. Kagawa et al., J. Pharm. Exp. Ther., 126, 123 (1959). In this test male albino rats (150–160 g) are kept under laboratory conditions for four days, after which they are bilaterally adrenalectomized under diethyl ether anesthesia. The animals are then maintained for 48 hours on a diet of rat chow (Purina Rat Chow) and 5% (W/V) glucose solution (ad libitum). Prior to the test the animals are starved for eighteen hours, but are allowed access to the 5% (W/V) glucose solution. Each rat then receives a single subcutaneous injection of physiological saline (2.5 ml), followed by a subcutaneous injection of desoxycorticosterone acetate (DOCA, 12.5 mcg per rat). The test compounds are administered orally. The rats are placed in metabolism cages and the urine is collected for four hours. Urine volume and urinary sodium, potassium and chloride are measured. The compounds of this invention show a dose response dependency for antialdosterone activity in the range of 1.0 to 100 mg/kg of body weight. More specifically, this test shows that the following representative compounds of of formula I are effective diuretic agents by increasing the urine volume and sodium and chloride excretion without affecting potassium excretion (the effective oral dose in mg per kilogram of body weight is indicated in the parentheses): 1,2,6-triphenyl-1,4,5,6-tetrahydropyrimidine (5 mg, described in Example 9), 2-methyl-1,6-diphenyl-1,4,5,6-tetrahydropyrimidine (5 mg, described in Example 62), 1,6-diphenyl-2-(3,4-dimethoxyphenyl)-1,4,5,6-tetrahydropyrimidine (5 mg, described in Example 63), 2-(2-thienyl)-1,6-diphenyl-1,4,5,6-tetrahydropyrimidine (1 mg, described in Example 66) and 1,6-diphenyl-2-(3-pyridinyl)-1,4,5,6-tetrahydropyrimidine (25 mg, described in Example 77).

Another test for antialdosterone diuretic activity, described by C. M. Kagawa et al., Arch. Pharmacodyn. Ther., 149, 8 (1964), is conducted in intact female dogs. The dogs are given 0.25 mg of DOCA in 0.25 ml of sesame oil intramuscularly and the test drug orally by capsule two hours before the beginning of infusion. A retention catheter is placed in the bladder for urine collection, and the cephalic vein is cannulated for infusion. Saline, 0.45%, plus dextrose, 5%, is infused intravenously at a rate of 1 ml/kg/min for 20 minutes, after which the rate is reduced to 0.3 ml/kg/min for the duration of the experiment. Urine is collected at 30 minute intervals, the urine volumes are recorded, and samples are taken. Collections are continued for five 30 minute periods. The urine samples are analyzed and the urinary Na/K ratios are calculated. This test shows that the following representative compounds of formula I are effective diuretic agents by increasing the urine volume and sodium and chloride excretion without affecting potassium excretion (the effective oral dose in mg per kilogram of body weight is indicated in the parentheses): 2-methyl-1,6-diphenyl-1,4,5,6-tetrahydropyrimidine (1.0 mg, described in Example 62), 1,6-diphenyl-2-(3,4-dimethoxyphenyl)-1,4,5,6-tetrahydropyrimidine (5 mg, described in Example 63) and 2-(2-thienyl)-1,6-diphenyl-1,4,5,6-tetrahydropyrimidine (15 mg, described in Example 66).

The compounds of formula I can be also administered to a mammal in a combination with a therapeutically effective dose of diuretic agent, acting by another mechanism. These latter diuretics, non-renal mineralocorticoid antagonizing diuretics, cause loss of water as well as the electrolytes: sodium, potassium, etc. Suitable diuretics for this combination, together with their dosage, are set out below:

| Diuretic | Recommended daily human dosage range (mg/70 Kg) |
| --- | --- |
| hydrochlorothiazide | 25–100 |
| chlorothiazide | 500–1000 |
| chlorthalidone | 50–200 |
| ethacrynic acid | 50–200 |
| furosemide | 40–80 |
| quinethazone | 50–100 |
| bumetanide | 1–2 |

The following method can be used to show that the combination of the compound of formula I with a diuretic agent can result in a useful reduction of potassium excretion while maintaining desired loss of water and sodium.

Male albino Sprague-Dawley rats weighing 180 to 200 g are divided into four groups of seven rats each. At the beginning of the test the bladder of each rat is emptied by gentle suprapubic pressure. The required dose of the compound of formula I and/or diuretic agent is suspended in 2% starch solution and administered orally. The control group receives the vehicle only. Each rat receives 5 ml. of 0.9% sodium chloride per gram of body weight orally. The rats are placed in individual metabolism cages and urine is collected for five hours after which the bladder is again emptied by gentle suprapubic pressure. All urine samples are analyzed for sodium, potassium and chloride content, and the sodium/potassium ratios are calculated.

The combination of a compound of formula I with other diuretic agents can be useful for treating certain indications, for instance, secondary hyperaldosteronism as result of a pathologic condition such as cirrhosis of the liver or as a result of overly vigorous diuretic therapy leading to hypokalemia. In addition, the use of a compound of formula I, given sequentially or simultaneously, in combination with another diuretic agent can allow the reduction of the dose of the other diuretic and still cause sufficient sodium excretion without excessive potassium loss.

While not wishing to be bound by any theory, it is believed that the diuretic effect of the compounds of formula I is primarily due to the antagonism of mineralocorticoids on renal electrolyte excretion and in part results from an additional direct renal tubular effect. The compounds of formula I are non-toxic when administered in effective diuretic amounts. In addition, since the compounds of formula I are non-steroidal, the compounds of formula I do not exhibit the undesirable side effects of steroidal antagonists of mineralocorticoids. Such common side effects of steroidal antagonists are gynecomastia and androgenic effects, i.e. hirsutism, irregular menses and deepening voice.

In addition to their use as diuretic agents, the compounds of formula I or a therapeutically acceptable acid addition salt thereof are useful agents for the treatment of hypertension in a mammal. For the treatment of hypertension in a mammal, the compounds of formula I are administered in the same manner as described herein for their use as diuretic agents. When used for the treatment of hypertension, the compound of formula I can be administered alone or administered sequentially or simultaneously in combination with an effective amount of a non-mineralocorticoid antagonizing diuretic agent. Furthermore, a combination of an antihypertensive effective amount of an antihypertensive agent with the compound of formula I or a thereapeutically acceptable acid addition salt thereof or a combination of an antihypertensive effective amount of an antihypertensive agent with the compound of formula I or a therapeutically acceptable acid addition salt thereof and an effective amount of a non-mineralocorticoid antagonizing diuretic agent is useful for the treatment of hypertension in a mammal. Suitable antihypertensive agents for use in this combination can be selected from Rauwolfia and related alkaloids e.g. reserpine, syrosingopine, deserpidine, rescinnamine; guanethidines, e.g. guanethidine, 2-heptamethylineimino-ethylguanidine or related guanidines covered in U.S. Pat. No. 2,928,829 by R. P. Mull, issued Mar. 15, 1960, herein incorporated by reference; veratrum alkaloids, e.g. protoveratrines A and B or germine; hydralazine; diazoxide; minoxidil; nitroprusside; phentolamine; phenoxybenzamine; pargyline; chlorisondamine; hexamethonium; mecamylamine; pentoliniuium; trimethaphan; clonidine; methyldopa; and propranolol. A combination of antihypertensive agents, for example reserpine and hydralazine, can be substituted for a single antihypertensive agent, as described above. Suitable methods of administration, compositions and dosages of the above described antihypertensive agents are described in medical textbooks, for instance, see Charles E. Baker, Jr. "Physician's desk reference", Medical Economies Company, Oradell, N.J., 1977. For example, the antihypertensive agent propranolol is administered orally as propranolol hydrochloride (INDERAL) to humans in the effective dose range of 80 to 640 mg per day. The compounds of formula I, when administered in combination with an antihypertensive agent or an antihypertensive agent plus a non-mineralocorticoid antagonizing diuretic agent for the treatment of hypertension, are used in the same manner as described herein for their use as diuretic agents.

When the compounds of formula I of this invention are used as diuretic and/or antialdosterone agents in mammals, e.g rats and dogs, they are used alone or in combination with pharmacologically acceptable carriers, the proportion of which is determined by the solubility and chemical nature of the compound, chosen route of administration and standard biological practice. For example, they are administered orally in solid form i.e. capsule or tablet. They are also administered orally in the form of suspensions or solutions or they may be injected parenterally. For parenteral administration they may be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of the invention contain the active ingredient in admixture with one or more non-toxic pharmaceutical excipients known to be suitable in the manufacture of aqueous suspensions. Suitable excipients are, for example, methyl-cellulose, sodium alginate, gum accacia, lecithin and so forth. The aqueous suspension can also contain one or more perservatives, one or more colouring agents and/or one or more sweetening agents.

Non-aqueous suspensions can be formulated by suspending the active ingredient in a vegetable oil, for example, arachic oil, olive oil, sesame oil, or coconut oil; or in mineral oil. The suspension can contain a thickening agent, for example beeswax, hard paraffin or cetyl alcohol. These compositions can also contain a sweetening agent, flavouring agent and antioxidant.

The dosage of the compounds of formula I of this invention as diuretic and antialdosterone agents will vary with the form of administration and the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective diuretic and antialdosterone amount of the compounds usually ranges from about 1.0 mg to about 500 mg per kilogram of body weight per day, although as aforementioned variations will occur. However a dosage level that is in range of from about 5 mg to about 300 mg per kilogram of body weight per day is employed most desirably in order to achieve effective results.

PROCESS

For the preparation of the 1,4,5,6-tetrahydropyrimidine derivatives, the preferred starting materials are the 1,3-propanediamine derivatives of formula III $$R^2-NH-CH(R^1)CH_2CH_2-NH_2 \qquad (III)$$

in which $R^1$ and $R^2$ each is phenyl or phenyl monosubstituted with lower alkyl, halo or lower alkoxy. The starting materials of formula III are either known or they can be obtained by methods described by A. N. Kost et al., Probl. Organ. Sinteza, Akad. Nauk SSSR, Otd. Obshch. i. Tekhn. Khim. 1965, 182 (Russ), see Chem. Abstr., 64, 9702 h (1966), and K. D. Hesse, Justus Liebigs Ann. Chem., 743, 50 (1971). Reaction scheme 1 illustrates the preferred method for the preparation of the 1,3-propanediamine derivatives of formula III.

Reaction Scheme 1

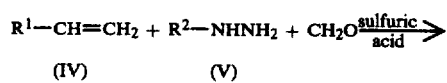

(IV)    (V)

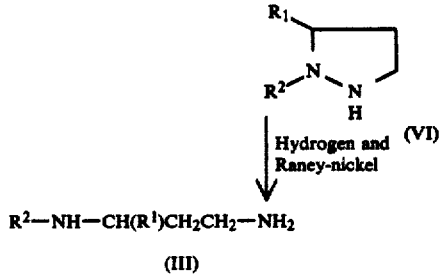

$$R^2-NH-CH(R^1)CH_2CH_2-NH_2 \quad \text{(III)}$$

With reference to reaction scheme 1, the Mannich-type condensation of an appropriate styrene of formula IV, an appropriate phenylhydrazine of formula V and formaldehyde in a strongly acidic medium gives the corresponding pyrazolidine derivative of formula VI. Catalytic hydrogenation of the latter compound in the presence of Raney-nickel gives the corresponding 1,3-propanediamine derivative of formula III.

The 1,3-propanediamine of formula III is acylated to form the corresponding compound of formula II $$R^2-NH-CH(R^1)CH_2CH_2-NH-COR^3 \quad \text{(II)}$$

in which $R^1$, $R^2$ and $R^3$ are as defined herein. This acylation is readily achieved by a variety of acylation methods.

The preferred method for the preparation of the compound of formula III is the acylation of the 1,3-propanediamine of formula III with an acyl chloride of formula $R^3$—CO—Cl in which $R^3$ is as defined herein. For this acylation, the 1,3-propanediamine of formula III is reacted with one to two molar equivalents, preferably 1.1 molar equivalents, of an acyl chloride of formula $R^3$—CO—Cl in the presence of 7 to 12 molar equivalents of an inorganic proton acceptor, preferably sodium or potassium hydroxide, at 0° to 10° C. for 10 to 100 minutes. Suitable solvents for this reaction are composed of a mixture of water and a water immiscible inert organic solvent, preferably methylene chloride, chloroform and the like.

Another acylation method for preparing the compound of formula II is the direct acylation of the 1,3-propanediamine of formula III with three to seven molar equivalents of a carboxylic acid of formula $R^3$—COOH at 100° to 150° C. for 15 to 40 hours in an inert organic solvent, preferably toluene, xylene and the like.

Still another method for preparing the compound of formula III is the acylation of the 1,3-propanediamine of formula III using a mixed anhydride prepared from a carboxylic acid of formula $R^3$—COOH. The mixed anhydride of the carboxylic acid is prepared by reacting about 1.5 molar equivalents of ethyl chloroformate and about 0.90 molar equivalents of the carboxylic acid of formula $R^3$—COOH in the presence of an organic proton acceptor, preferably triethylamine, in an inert organic solvent, preferably tetrahydrofuran, at 0° to 20° C. for 10 to 40 minutes.

The latter solution is then added to a solution of about one molar equivalent of the 1,3-propanediamine of formula III in an inert organic solvent, preferably tetrahydrofuran and the resulting solution is stirred at 20° to 70° C. for one to five hours.

If desired, the above described compounds of formula II in which $R^1$ and $R^2$ are as defined herein and $R^3$ is a radical of formula $R^4$—A wherein A is as defined herein and $R^4$ is chloro or bromo can be aminated to obtain the corresponding compound of formula II in which $R^1$ and $R^2$ are as defined herein and $R^3$ is a radical of formula $R^4$—A wherein A is as defined herein and $R^4$ is lower alkylamino, di(lower alkyl)amino, 1-piperidinyl or 4-morpholinyl. A useful amination method is to react the compound of formula II in which $R^1$ and $R^2$ are as defined herein and $R^3$ is a radical of formula $R^4$—A wherein A is as defined herein and $R^4$ is chloro or bromo with 1.1 to 2.0 molar equivalents of a lower alkylamine, di(lower alkyl)amine, piperidine or morpholine in the presence of an inorganic proton acceptor, preferably sodium or potassium hydroxide, in an inert solvent, for example a lower alkanol, preferably methanol and/or ethanol, at 20° to 30° C. for 15 to 40 hours. Another useful amination method is to react the latter described compound of formula II with about 10 to 100 molar equivalents of a lower alkylamine, di(lower alkyl)amine, piperidine or morpholine at 20° to 40° C. for 15 to 40 hours (i.e. no solvent is required).

Although a number of methods for the cyclization of 1,3-propanediamine derivatives to obtain the 1,4,5,6-tetrahydropyrimidine nucleus are described in the prior art, none of prior art methods is generally practical for the preparation of the compounds of formula I of this invention. In order to overcome this problem, the process, as described herein, for the cyclization of the compound of formula II to give the corresponding compound of formula I in which $R^1$, $R^2$ and $R^3$ are defined herein, is novel and practical. The compound of formula II is readily cyclized using phosphorus oxychloride. For this cyclization about one to five, preferably two to three, molar equivalents of phosphorus oxychloride usually are employed. A suitable dry inert organic solvent, for example benzene, dioxane, toluene and xylene, preferably is used as a reaction medium. The cyclization reaction is conducted at 80° to 200° C., preferably at 100° to 150° C., for one to ten hours, preferably for two to six hours, and the compound of formula I is isolated by standard techniques, for instance, see the examples.

If desired, the above described compounds of formula I in which $R^1$ and $R^2$ are as defined herein and $R^3$ is a radical of formula $R^4$—A wherein A is as defined herein and $R^4$ is chloro or bromo can be aminated with a di(lower alkyl)amine, piperidine or morpholine, in the same manner as described above for the amination of the compound of formula II in which $R^4$ is chloro or bromo, to obtain the corresponding compound of formula I in which $R^1$ and $R^2$ are as defined herein and $R^3$ is a radical of formula $R^4$—A wherein A is as defined herein and $R^4$ is di(lower alkyl)amino, 1-piperidinyl or 4-morpholinyl.

The following examples illustrate further this invention.

EXAMPLE 1

2,3-Diphenylpyrazolidin (VI; $R^1$ and $R^2 = C_6H_5$)

Phenylhydrazine (108.14 g, 1 mole) is added dropwise to a cooled (4°-8° C.) and stirred mixture of concentrated sulfuric acid (147 g, 1.5 moles), glacial acetic acid (200 ml) and water (25 ml). Paraformaldehyde (30.03 g, 1 mole) and phenylethylene (104.1 g, 1 mole) are added simultaneously during 1 hr at 25° C. and stirring is continued for 2 hr at 30° C. Water (500 ml) is added and the aqueous dark solution is washed with benzene. The aqueous layer is basified with 50% sodium hydroxide and extracted with benzene. The organic extracts are combined, dried over magnesium sulfate and evaporated. The residue is distilled at 170° C. 0.6 torr to give a distillate of the title compound (135.9 g). The title compound is dissolved in diethyl ether and dry hydrogen chloride is added. The precipitate is collected and crystallized from methanol-diethyl ether to obtain the hydrochloride salt of the title compound, mp 212°–214° C.

Anal: Calcd. for $C_{15}H_{17}ClH_2$: C, 69.09; H, 6.57; N, 10.75%. Found: C, 68.89; H, 6.74; N, 10.61%.

EXAMPLE 2

N,1-Diphenyl-1,3-propanediamine (III; $R^1$ and $R^2=C_6H_5$)

2,3-Diphenylpyrazolidin (133.9 g, 620 mmoles, described in Example 1) is dissolved in methanol (1.7 liters) and the solution is heated at 60° C. in the presence of Raney nickel (37 g) under 50 atmospheres of hydrogen for 5 hr. The catalyst is removed by filtration through diatomaceous earth and the filtrate is evaporated. The residue is crystallized from cyclohexane-hexane to give the title compound (48.4 g) mp 104°–105° C.

By following the procedure of Examples 1 and 2, but replacing phenylhydrazine in Example 1 with an equivalent amount of 2-methylphenylhydrazine, 4-pentylphenylhydrazine, 3-chlorophenylhydrazine, 4-iodophenylhydrazine, 2-ethoxyphenylhydrazine or 3-(1-methylethyl)phenylhydrazine, the following compounds of formula III are obtained, respectively: N-(2-methylphenyl)-1-phenyl-1,3-propanediamine, N-(4-pentylphenyl)-1-phenyl-1,3-propanediamine, N-(3-chlorophenyl)-1-phenyl-1,3-propanediamine, N-(4-iodophenyl)-1-phenyl-1,3-propanediamine, N-(2-ethoxyphenyl)-1-phenyl-1,3-propanediamine, and N-[3-(1-methylethyl)phenyl]-1-phenyl-1,3-propanediamine.

Similarly, but replacing phenylethylene with an equivalent amount of 3-butylphenylethylene, 4-bromophenylethylene or 4-pentoxyphenylthylene, the following compounds of formula III are obtained, respectively: N-phenyl-1-(3-butylphenyl)-1,3-propanediamine, N-phenyl-1-(4-bromophenyl)-1,3-propanediamine and N-phenyl-1-(4-pentoxyphenyl)-1,3-propanediamine.

EXAMPLE 3

N-[3-Phenyl-3-(phenylamino)propyl]benzamide (II; $R^1$, $R^2$ and $R^3=C_6H_5$)

A solution of N,1-diphenyl-1,3-propanediamine (5.0 g, 22 mmoles, described in Example 2) and benzoic acid (12.5 g, 105 mmoles) in dry xylene (300 ml) is refluxed for 20 hr using a Dean-Stark water separator. The mixture is cooled and washed with several portions of 2 N hydrochloric acid. The aqueous extracts are combined, basified with dilute sodium hydroxide and extracted with chloroform. The organic extract is washed with brine, dried over magnesium sulfate and evaporated. The residue is chromatographed an silica gel using chloroform and the eluates are evaporated. The residue is crystallized from benzene-hexane to obtain the title compound (2.0 g), mp 120°–121° C.

Anal: Calcd. for $C_{22}H_{22}N_2O$: C, 79.97; H, 6.71; N, 8.48%. Found: C, 80.29; H, 6.79; N, 8.45%.

In the same manner but replacing benzoic acid with an equivalent amount of 3-methoxyphenylacetic acid or propionic acid, the following compounds of formula II are obtained, respectively: N-[3-phenyl-3-(phenylamino)propyl]-2-(3-methoxyphenyl)-acetamide, mp 90°–92° C., and N-[3-phenyl-3-(phenylamino)-propyl]propionamide, mp 102°–103° C.

In the same manner but replacing N,1-diphenyl-1,3-propanediamine with an equivalent amount of another compound of formula III described in Example 2, the following compounds of formula II are obtained, respectively: N-[3-phenyl-3-[(2-methylphenyl)amino]propyl]benzamide, N-[3-phenyl-3-[(4-pentylphenyl)amino]propyl]benzamide, N-[3-phenyl-3-[(3-chlorophenyl)amino]propyl]benzamide, N-[3-phenyl-3-[(4-iodophenyl)amino]benzamide, N-[3-phenyl-3-[(2-ethoxyphenyl)amino]propyl]benzamide, N-[3-phenyl-3-[[3-(1-methylethyl)phenyl]amino]propyl]benzamide, N-[3-(3-butylphenyl)-3-(phenylamino)propyl]benzamide, N-[3-(4-bromophenyl)-3-(phenylamino)propyl]benzamide and N-[3-(4-pentoxyphenyl)-3-(phenylamino)propyl]benzamide.

EXAMPLE 4

N-[3-Phenyl-3-(phenylamino)propyl]chloroacetamide (II; $R^1$ and $R^2=C_6H_5$ and $R^3=CH_2Cl$)

Chloroacetyl chloride (5.0 g, 3.6 ml, 44.6 mmoles) is added dropwise to a cooled mixture (4°–8° C.) of N,1-diphenyl-1,3-propanediamine (10.0 g, 44.2 mmoles, described in Example 2) in methylene chloride (200 ml) and 8 N sodium hydroxide (50 ml). After the addition, the mixture is stirred for 30 min. The aqueous phase is separated and extracted with methylene chloride. The methylene chloride solutions are combined, washed with brine, dried over magnesium sulfate and evaporated. The residue is chromatographed on silica gel using chloroform and the eluates are evaporated. The residue is crystallized from diethyl ether to obtain the title compound (3.7 g), mp 65°–68° C.

Anal: Calcd. for $C_{17}H_{19}ClN_2O$: C, 67.42; H, 6.32; N, 9.25%. Found: C, 67.31; H, 6.36; N, 9.55%.

In the same manner but replacing chloroacetyl chloride with an equivalent amount of 3-chloropropionyl chloride, 3-chloro-2,2-dimethylpropionyl chloride or 4-chlorobutanoyl chloride, the following compounds of formula II are obtained, respectively: N-[3-phenyl-3-(phenylamino)propyl]-3-chloropropionamide, mp 87°–88° C., N-[3-phenyl-3-(phenylamino)propyl]-3-chloro-2,2-dimethylpropionamide, mp 75°–77° C., and N-[3-phenyl-3-(phenylamino)propyl]-4-chlorobutanamide, mp 74°–76° C.

In the same manner but replacing N,1-diphenyl-1,3-propanediamine with an equivalent amount of another compound of formula III described in Example 2, the following compounds of formula II are obtained, respectively: N-[3-phenyl-3-[(2-methylphenyl)amino]propyl]chloroacetamide, N-[3-phenyl-3-[(4-pentylphenyl)amino]propyl]chloroacetamide, N-[3-phenyl-3-[(3-chlorophenyl)amino]propyl]chloroacetamide, N-[3-phenyl-3-[(4-iodophenyl)amino]propyl]chloroacetamide, N-[3-phenyl-3-[(2-ethoxyphenyl)amino]propyl]chloroacetamide, N-[3-phenyl-3-[[3-(1-methylethyl)phenyl]amino]propyl]chloroacetamide, N-[3-(3-butylphenyl)-3-(phenylamino)propyl]chloroacetamide, N-[3-(4-bromophenyl)-3-(phenylamino)propyl]chloroacetamide and N-[3-(4-pentoxyphenyl)-3-(phenylamino)propyl]chloroacetamide.

EXAMPLE 5

N-[3-Phenyl-3-(phenylamino)propyl]dimethylaminoacetamide (II; $R^1$ and $R^2 = C_6H_5$ and $R^3 = CH_2N(CH_3)_2$)

A solution of N-[3-phenyl-3-(phenylamino)propyl]chloroacetamide (2.90 g, 9.6 mmoles described in Example 4) in methanol (10 ml) is added dropwise to a mixture of dimethylamine hydrochloride (1.2 g, 14.8 mmoles) and potassium hydroxide (1.1 g) in ethanol (35 ml). The mixture is stirred at room temperature (20° C.) for 18 hr and filtered. The filtrate is evaporated and the residue is dissolved in methylene chloride. The solution is washed with brine, dried over magnesium sulfate and evaporated. The residue is chromatographed on silica gel with 1:50 methanol-chloroform solvent combination and the eluates are evaporated. The residue is crystallized from benzene-hexane to give the title compound (0.90 g), mp 82° C.

Anal: Calcd. for $C_{19}H_{25}N_3O$: C, 73.28; H, 8.09; N, 13.49%. Found: C, 73.29; H, 8.09; N, 13.56%.

EXAMPLE 6

N-[3-Phenyl-3-(phenylamino)propyl]-2-(1-piperidinyl)acetamide (II; $R^1$ and $R^2 = C_6H_5$ and $R^3 = $ 1-piperidinylmethyl)

A solution of N-[3-phenyl-3-(phenylamino)]chloroacetamide (1.60 g, 5.27 mmoles, described in Example 4) in piperidine (10 g) is allowed to stand 18 hr at room temperature and filtered. The filtrate is evaporated and the residue is dissolved in methylene chloride. The solution is washed with dilute sodium hydroxide, brine, dried over magnesium sulfate and evaporated. The residue is crystallized from benzenehexane to give the title compound (0.90 g), mp 108°–111° C.

Anal: Calcd for $C_{22}H_{29}N_3O$: C, 75.17; H, 8.32; N, 11.96%. Found: C, 74.84; H, 8.23; N, 12.21%.

In the same manner but replacing N-[3-phenyl-3-(phenylamino)propyl]chloroacetamide with an equivalent amount of another compound of formula II, described in Example 4, the following compounds of formula II are obtained respectively: N-[3-phenyl-3-(phenylamino)propyl]-3-(1-piperidinyl)propionamide, N-[3-phenyl-3-(phenylamino)propyl]-3-[(1-piperidinyl)-2,2-dimethyl]propionamide, N-[3-phenyl-3-(phenylamino)propyl]-4-(1-piperidinyl)butanamide, N-[3-phenyl-3-[(2-methylphenyl)amino]propyl]-2-(1-piperidinyl)acetamide, N-[3-phenyl-3-[(4-pentylphenyl)amino]propyl]-2-(1-piperidinyl)acetamide, N-[3-phenyl-3-[(3-chlorophenyl)amino]propyl]-2-(1-piperidinyl)acetamide, N-[3-phenyl-3-[(4-iodophenyl)amino]propyl]-2-(1-piperidinyl)acetamide, N-[3-phenyl-3-[(2-ethoxylphenyl)amino]propyl]-2-(1-piperidinyl)acetamide, N-[3-phenyl-3-[[3-(1-methylethyl)phenyl]amino]propyl]-2-(1-piperidinyl)acetamide, N-[3-(3-butylphenyl)-3-(phenylamino)propyl]-2-(1-piperidinyl)acetamide, N-[3-(4-bromophenyl)-3-(phenylamino)propyl]-2-(1-piperidinyl)acetamide and N-[3-(4-pentoxyphenyl)-3-(phenylamino)propyl]-2-(1-piperidinyl)acetamide.

Similarly, but replacing piperidine with an equivalent amount of morpholine and using a compound of formula II, described in Example 4, the following compounds of formula II are obtained, respectively: N-[3-phenyl-3-(phenylamino)propyl]-2-(4-morpholinyl)acetamide, mp 69°–70° C., N-[3-phenyl-3-(phenylamino)propyl]-3-(4-morpholinyl)propionamide, mp 105°–106° C., N-[3-phenyl-3-(phenylamino)propyl]-3-[(4-morpholinyl)-2,2-dimethyl]propionamide, N-[3-phenyl-3-(phenylamino)propyl]-4-(4-morpholinyl)butanamide, N-[3-phenyl-3-[(2-methylphenyl)amino]propyl]-2-(4-morpholinyl)acetamide, N-[3-phenyl-3-[(4-pentylphenyl)amino]propyl]-2-(4-morpholinyl)acetamide, N-[3-phenyl-3-[(3-chlorophenyl)amino]propyl]-2-(4-morpholinyl)acetamide, N-[3-phenyl-3-[(4-iodophenyl)amino]propyl]-2-(4-morpholinyl)acetamide, N-[3-phenyl-3-[(2-ethoxylphenyl)amino]propyl]-2-(4-morpholinyl)acetamide, N-[3-phenyl-3-[[3-(1-methylethyl)phenyl]amino]propyl]-2-(4-morpholinyl)acetamide, N-[3-(3-butylphenyl)-3-(phenylamino)propyl]-2-(4-morpholinyl)acetamide, N-[3-(4-bromophenyl)-3-(phenylamino)propyl]-2-(4-morpholinyl)acetamide and N-[3-(4-pentoxyphenyl)-3-(phenylamino)propyl]-2-(4-morpholinyl)acetamide.

EXAMPLE 7

N-[3-Phenyl-3-(phenylamino)propyl]-2,2-dimethylpropionamide (II; $R^1$ and $R^2 = C_6H_5$ and $R^3 = C(CH_3)_3$)

A solution of N,1-diphenyl-1,3-propanediamine (6.00 g, 26.5 mmoles, described in Example 2) in methylene chloride (70 ml) is stirred at 0°–5° C. in the presence of aqueous 2.5 N sodium hydroxide (40 ml) and 2,2-dimethylpropanoyl chloride (3.20 g, 26.6 mmoles) is added dropwise to the stirred mixture. The mixture is stirred for 15 min. The organic layer is separated, washed with brine, dried over magnesium sulfate and evaporated. The residue is crystallized from ethyl acetate-hexane to give the title compound (6.77 g), mp 107°–108° C.

Anal: Calcd for $C_{20}H_{26}N_2O$: C, 77.38; H, 8.44; N, 9.03%. Found: C, 77.10; H, 8.48; N, 9.00%.

In the same manner but replacing 2,2-dimethylpropanoyl chloride with an equivalent amount of acetyl chloride, 3,4-dimethoxybenzoyl chloride, 3-phenyl-2-propenoyl chloride, 2-furoyl chloride, 2-thiophenecarbonyl chloride or dimethylcarbamyl chloride, the following compounds of formula are obtained, respectively: N-[3-phenyl-3-(phenylamimo)propyl]acetamide, mp 97°–98° C.; N-[3-phenyl-3-(phenylamino)propyl]-(3,4-dimethoxy)benzamide, nmr (CDCl₃) δ 2.14 (q), 3.60 (q), 3.83(s), 3.87(s), 4.50(t) and 6.40–7.60(m); N-[3-phenyl-3-(phenylamimo)propyl]-3-phenyl-2-propenamide, mp 139°–141° C.; N-[3-phenyl-3-(phenylamino)propyl]-2-furamide, nmr (CDCl₃) δ 2.10(q), 3.52(q), 4.45(t), 4.55(s) and 6.30–7.70(m); N-[3-phenyl-3-(phenylamino)propyl]-2-thiophenecarboxamide, nmr (CDCl₃) δ 2.20(q), 3.52(q), 4.33(t), 6.02(s) and 6.50–810(m); and 1,1-dimethyl-3-[3-phenyl-3-(phenylamino)propyl]urea, mp 96°–97.5° C.

In the same manner but replacing N,1-diphenyl-1,3-propanediamine with an equivalent amount of another compound of formula III described in Example 2, the following compounds of formula II are obtained, respectively: N-[3-phenyl-3-[(2-methylphenyl)amino]propyl]-2,2-dimethylpropionamide, N-[3-phenyl-3-[(4-pentylphenyl)amino]propyl]-2,2-dimethylpropionamide, N-[3-phenyl-3-[(3-chlorophenyl)amino]propyl]-2,2-dimethylpropionamide, N-[3-phenyl-3-[(4-iodophenyl)amino]propyl]-2,2-dimethylpropionamide, N-[3-phenyl-3-[(2-ethoxylphenyl)amino]propyl]-2,2-dimethylpropionamide, N-[3-phenyl-3-[[3-(1-methylethyl)phenyl]propyl]-2,2-dimethylpropionamide, N-[3-(3-butylphenyl)-3-(phenylamino)propyl]-2,2-dimethylpropionamide, N-[3-(4-bromophenyl)-3-(phenylamino)propyl]-2,2-dimethylpropionamide and N-[3-(4-pentoxyphenyl)-3-(phenylamino)propyl]-2,2-dimethylpropionamide.

EXAMPLE 8

N-[3-Phenyl-3-(phenylamino)propyl]pyridin-3-ylcarboxamide(II; $R^1$ and $R^2=C_6H_5$ and $R^3=$3-pyridinyl)

Ethyl chloroformate (9.6 ml, 98.6 mmoles) is added dropwise to a solution at 0° C. of triethylamine (14 ml, 101 mmole), pyridine-3-ylcarboxylic acid (7.4 g, 60 mmoles) in dry tetrahydrofuran (100 ml). The mixture is stirred at 15° C. for 30 min and filtered. The filtrate is added dropwise to a solution of N,1-diphenyl-1,3-propanediamine (15.0 g, 66.3 mmoles, described in Example 2) in tetrahydrofuran (50 ml), the mixture is stirred one hr at room temperature and refluxed for 30 min. The mixture is evaporated and the residue is chromatographed on a column of silica gel using methanol-chloroform (1:10). The eluates are evaporated and the residue (12.6 g) is crystallized from benzene-hexane to obtain the title compound, mp 79°–81° C.

In the same manner but replacing N,1-diphenyl-1,3-propanediamine with an equivalent amount of another compound of formula III described in Example 2, the following compounds of formula II are obtained, respectively: N-[3-phenyl-3-[(2-methylphenyl)amino]propyl]-pyridine-3-ylcarboxamide, N-[3-phenyl-3-[(4-pentylphenyl)amino]propyl]pyridine-3-ylcarboxamide, N-[3-phenyl-3-[(3-chlorophenyl)amino]propyl]pyridine-3-ylcarboxamide, N-[3-phenyl-3-[(4-iodophenyl)amino]propyl]pyridine-3-ylcarboxamide, N-[3-phenyl-3-[(2-ethoxylphenyl)amino]propyl]pyridine-3-ylcarboxamide, N-[3-phenyl-3-[[3-(1-methylethyl)phenyl]amino]propyl]pyridin-3-ylcarboxamide, N-[3-(3-butylphenyl)-3-(phenylamino)propyl]pyridin-3-ylcarboxamide, N-[3-(4-bromophenyl)-3-(phenylamino)propyl]pyridin-3-ylcarboxamide and N-[3-(4-pentoxyphenyl)-3-(phenylamino)propyl]pyridin-3-ylcarboxamide.

EXAMPLE 9

1,2,6-Triphenyl-1,4,5,6-tetrahydropyrimidine (I; $R^1$, $R^2$ and $R^3=C_6H_5$)

A solution of N-[3-phenyl-3-(phenylamino)propyl]-benzamide (12.0 g, 36.3 mmoles described in Example 3) in dry toluene (250 ml) is refluxed in the presence of phosphorus oxychloride (12.5 g, 7.5 ml, 81.5 mmoles) for 5 hr. The solution is evaporated and the residue is dissolved in methylene chloride. The latter solution is washed with aqueous sodium hydroxide, brine, dried over magnesium sulfate and evaporated to give a residue (9.3 g) of the title compound, nmr (CDCl₃) δ 2.1(m), 3.5(m), 4.88(t) and 7.1(m). The title compound is dissolved in methanol, hydrogen bromide is bubbled into the solution and diethyl ether is added until no additional precipitate forms. The precipitate is collected and crystallized from methanol-diethyl ether to obtain the hydrobromide salt (7.5 g) of the title compound, mp 292°–295° C.

Anal: Calcd for $C_{22}H_{21}N_2Br$: C, 67.19; H, 5.38; N, 7.13%. Found: C, 67.55; H, 5.44; N, 7.38%.

In the same manner but replacing toluene with dioxane or xylene, the title compound is obtained.

By following the procedure of Example 9 using the appropriate starting material of formula, other compounds of formula I are obtained. Examples of such compounds of formula I are listed as products in Table 1 together with the appropriate starting material of formula II used for the preparation of the compound of formula I. In each case the compound of formula II is noted by the number of the example in which it is prepared.

TABLE 1

| | Starting Material of Formula II | | | | Product: [(prefix listed below)-1,4,5,6-tetrahydropyrimidine] |
|---|---|---|---|---|---|
| Example | $R^1$ | $R^2$ | $R^3$ | Described in Example | Prefix |
| 10 | Ph | Ph | (3-MeO—Ph)—CH₂ | 3 | 1,6-diphenyl-2-(3-methoxyphenylmethyl), nmr (CDCl₃) δ 3.57(s) |
| 11 | Ph | Ph | C₂H₅ | 3 | 1,6-diphenyl-2-ethyl, nmr (CDCl₃) δ 1.25(t), 2.67(q) and 4.80(m) |
| 12 | Ph | 2-Me—Ph | Ph | 3 | 2,6-diphenyl-1-(2-methylphenyl) |
| 13 | Ph | 3-(C₅H₁₁)—Ph | Ph | 3 | 2,6-diphenyl-1-(4-pentylphenyl) |
| 14 | Ph | 3-Cl—Ph | Ph | 3 | 2,6-diphenyl-1-(3-chlorophenyl) |
| 15 | Ph | 4-I—Ph | Ph | 3 | 2,6-diphenyl-1-(4-iodophenyl) |
| 16 | Ph | 2-EtO—Ph | Ph | 3 | 2,6-diphenyl-1-(2-ethoxyphenyl) |
| 17 | Ph | 3-Me₂CH—Ph | Ph | 3 | 2,6-diphenyl-1-[3-(1-methylethyl)phenyl] |
| 18 | 3-Bu—Ph | Ph | Ph | 3 | 1,2-diphenyl-6-(3-butylphenyl) |
| 19 | 4-Br—Ph | Ph | Ph | 3 | 1,2-diphenyl-6-(4-bromophenyl) |
| 20 | 4-C₅H₁₁—O—Ph | Ph | Ph | 3 | 1,2-diphenyl-6-(4-pentoxyphenyl) |
| 21 | Ph | Ph | Cl—CH₂ | 4 | 2-chloromethyl-1,6-diphenyl, nmr (DMSO—D₆) δ 2.2(m), 3.5(m), 4.3(s), 5.1(m) and 7.35(m) |
| 22 | Ph | Ph | Cl—CH₂CH₂ | 4 | 2-(2-chloroethyl)-1,6-diphenyl |
| 23 | Ph | Ph | Cl—CH₂—C(Me)₂ | 4 | 2-[(2-chloro-1,1-dimethyl)ethyl]-1,6-diphenyl, nmr (CDCl₃) δ 1.3(s), 1.48(s), 2.5–3.5(m), 4.0(d), 5.1(s), 5.15(m) and 7.1(s) |
| 24 | Ph | Ph | Cl—(CH₂)₃ | 4 | 2-[(3-chloropropyl)-1,6-diphenyl |
| 25 | Ph | 2-Me—Ph | Cl—CH₂ | 4 | 2-chloromethyl-6-phenyl-1-(2-methylphenyl) |
| 26 | Ph | 4-(C₅H₁₁)—Ph | Cl—CH₂ | 4 | 2-chloromethyl-6-phenyl-1-(4-pentylphenyl) |
| 27 | Ph | 3-Cl—Ph | Cl—CH₂ | 4 | 2-chloromethyl-6-phenyl-1-(3-chlorophenyl) |
| 28 | Ph | 4-I—Ph | Cl—CH₂ | 4 | 2-chloromethyl-6-phenyl-1-(4-iodophenyl) |
| 29 | Ph | 2-EtO—Ph | Cl—CH₂ | 4 | 2-chloromethyl-6-phenyl-1-(2-ethoxyphenyl) |
| 30 | Ph | 3-Me₂CH—Ph | Cl—CH₂ | 4 | 2-chloromethyl-6-phenyl-1-[3-(1-methylethyl)phenyl] |
| 31 | 3-Bu—Ph | Ph | Cl—CH₂ | 4 | 2-chloromethyl-1-phenyl-6-(3-butylphenyl) |
| 32 | 4-Br—Ph | Ph | Cl—CH₂ | 4 | 2-chloromethyl-1-phenyl-6-(4-bromophenyl) |
| 33 | 4-C₅H₁₁—O—Ph | Ph | Cl—CH₂ | 4 | 2-chloromethyl-1-phenyl-6-(4-pentoxyphenyl) |
| 34 | Ph | Ph | Me₂N—CH₂ | 5 | 2-(dimethylamino)methyl-1,6-diphenyl |
| 35 | Ph | Ph | 1-piperidinyl- | 6 | 1,6-diphenyl-2-(1-piperidinylmethyl), nmr(CDCl₃) |

TABLE 1-continued

| | Starting Material of Formula II | | | Described in Example | Product: [(prefix listed below)-1,4,5,6-tetrahydropyrimidine] Prefix |
|---|---|---|---|---|---|
| Example | R¹ | R² | R³ | | |
| | | | methyl | | δ 2.94(s), 2.65(m) and 7.06–7.13(m) and HBr salt mp 135–138° C. |
| 36 | Ph | Ph | 2-(1-piperidinyl)ethyl | 6 | 1,6-diphenyl-2-[2-(1-piperidinyl)ethyl] |
| 37 | Ph | Ph | 2-(1-piperdinyl)-1,1-dimethylethyl | 6 | 1,6-diphenyl-2-[2-(1-piperidinyl)-1,1-dimethylethyl] |
| 38 | Ph | Ph | 3-(1-piperidinyl)propyl | 6 | 1,6-diphenyl-2-[3-(1-piperidinyl)propyl] |
| 39 | Ph | 2-Me—Ph | 1-piperidinylmethyl | 6 | 6-phenyl-1-(2-methylphenyl)-2-(1-piperidinylmethyl) |
| 40 | Ph | 4-(C₅H₁₁)—Ph | 1-piperidinylmethyl | 6 | 6-phenyl-1-(4-pentylphenyl)-2-(1-piperidinylmethyl) |
| 41 | Ph | 3-Cl—Ph | 1-piperidinylmethyl | 6 | 6-phenyl-1-(3-chlorophenyl)-2-(1-piperidinylmethyl) |
| 42 | Ph | 4-I—Ph | 1-piperidinylmethyl | 6 | 6-phenyl-1-(4-iodophenyl)-2-(1-piperidinylmethyl) |
| 43 | Ph | 2-EtO—Ph | 1-piperidinylmethyl | 6 | 6-phenyl-1-(2-ethoxyphenyl)-2-(1-piperidinylmethyl) |
| 44 | Ph | 3-Me₂CH—Ph | 1-piperidinylmethyl | 6 | 6-phenyl-1-[3-(1-methylethyl)phenyl]-2-(1-piperidinylmethyl) |
| 45 | 3-Bu—Ph | Ph | 1-piperidinylmethyl | 6 | 1-phenyl-6-(3-butylphenyl)-2-(1-piperidinylmethyl) |
| 46 | 4-Br—Ph | Ph | 1-piperidinylmethyl | 6 | 1-phenyl-6-(4-bromophenyl)-2-(1-piperidinylmethyl) |
| 47 | 4-C₅H₁₁—O—Ph | Ph | 1-piperidinylmethyl | 6 | 1-phenyl-6-(4-pentoxyphenyl)-2-(1-piperidinylmethyl) |
| 48 | Ph | Ph | 4-morpholinylmethyl | 6 | 2-(4-morpholinylmethyl)-1,6-diphenyl |
| 49 | Ph | Ph | 2-(4-morpholinyl)ethyl | 6 | 2-[2-(4-morpholinyl)ethyl]-1,6-diphenyl |
| 50 | Ph | Ph | 2-(4-morpholinyl)-1,1-dimethylethyl | 6 | 2-[2-(4-morpholinyl)-1,1-dimethylethyl]-1,6-diphenyl |
| 51 | Ph | Ph | 3-(4-morpholinyl)propyl | 6 | 2-[3-(4-morpholinyl)propyl]-1,6-dipropyl |
| 52 | Ph | 2-Me—Ph | 4-morpholinylmethyl | 6 | 2-(4-morpholinylmethyl)-6-phenyl-1-(2-methylphenyl) |
| 53 | Ph | 4-(C₅H₁₁)—Ph | 4-morpholinylmethyl | 6 | 2-(4-morpholinylmethyl)-6-phenyl-1-(4-pentylphenyl) |
| 54 | Ph | 3-Cl—Ph | 4-morpholinylmethyl | 6 | 2-(4-morpholinylmethyl)-6-phenyl-1-(3-chlorophenyl) |
| 55 | Ph | 4-I—Ph | 4-morpholinylmethyl | 6 | 2-(4-morpholinylmethyl)-6-phenyl-1-(4-iodophenyl) |
| 56 | Ph | 2-EtO—Ph | 4-morpholinylmethyl | 6 | 2-(4-morpholinylmethyl)-6-phenyl-1-(2-ethoxyphenyl) |
| 57 | Ph | 3-Me₂CH—Ph | 4-morpholinylmethyl | 6 | 2-(4-morpholinylmethyl)-6-phenyl-1-[3-(1-methylethyl)phenyl] |
| 58 | 3-Bu—Ph | Ph | 4-morpholinylmethyl | 6 | 2-(4-morpholinylmethyl)-1-phenyl-6-(3-butylphenyl) |
| 59 | 4-Br—Ph | Ph | 4-morpholinylmethyl | 6 | 2-(4-morpholinylmethyl)-1-phenyl-6-(4-bromophenyl) |
| 60 | 4-C₅H₁₁—O—Ph | Ph | 4-morpholinylmethyl | 6 | 2-(4-morpholinylmethyl)-1-phenyl-6-(4-pentoxyphenyl) |
| 61 | Ph | Ph | Me₃C | 7 | 2-(1,1-dimethylethyl)-1,6-diphenyl, mp 118–119° C. |
| 62 | Ph | Ph | Me | 7 | 2-methyl-1,6-diphenyl, nmr (CDCl₃) δ 1.93(s), 2.3(s), 2.5(m), 3.5(m), 4.85(m), 7.08(m) and 5.9(s) and HBr salt mp 177–179° C. |
| 63 | Ph | Ph | 3,4-di(MeO)—Ph | 7 | 1,6-diphenyl-2-(3,4-dimethoxyphenyl), nmr (CDCl₃) δ 2.25(m), 3.50(m), 3.75(s), 5.00(t), 7.00(m) and 7.40(m) and HBr salt mp 195–196° C. |
| 64 | Ph | Ph | CH=CH—Ph | 7 | 2-(2-phenylethenyl)-1,6-diphenyl, nmr (CDCl₃) δ 2.25(m), 3.55(m), 4.92(t), 6.46(d), 7.51(d) and 7.30(m) and HBr salt mp 219–220° C. |
| 65 | Ph | Ph | 2-furyl | 7 | 2-(2-furyl)-1,6-diphenyl, nmr (CDCl₃) δ 2.10(m), 3.50(m), 4.80(m), 6.17(m) and 6.80–7.60(m) and HBr salt mp 206–208° C. |
| 66 | Ph | Ph | 2-thienyl | 7 | 2-(2-thienyl)-1,6-diphenyl, nmr (CDCl₃) δ 2.17(m), 3.57(m), 4.93(t), 6.81(d), 7.10(m) and 7.37(m) and HBr salt mp 260–261° C. |
| 67 | Ph | Ph | Me₂N | 7 | 2-dimethylamino-1,6-diphenyl, nmr (CDCl₃) δ 2.15(m), 2.69(s), 3.43(m), 4.74(t), 7.10(m) and 7.35(m) and HBr salt mp 165–167° C. |
| 68 | Ph | 2-Me—Ph | Me₃C | 7 | 2-(1,1-dimethylethyl)-6-phenyl-1-(2-methylphenyl) |
| 69 | Ph | 4-(C₅H₁₁)—Ph | Me₃C | 7 | 2-(1,1-dimethylethyl)-6-phenyl-1-(4-pentylphenyl) |
| 70 | Ph | 3-Cl—Ph | Me₃C | 7 | 2-(1,1-dimethylethyl)-6-phenyl-1-(3-chlorophenyl) |
| 71 | Ph | 4-I—Ph | Me₃C | 7 | 2-(1,1-dimethylethyl)-6-phenyl-1-(4-iodophenyl) |
| 72 | Ph | 3-EtO—Ph | Me₃C | 7 | 2-(1,1-dimethylethyl)-6-phenyl-1-(2-ethoxyphenyl) |
| 73 | Ph | 3-Me₂CH—Ph | Me₃C | 7 | 2-(1,1-dimethylethyl)-6-phenyl-1-[3-(1-methylethyl)phenyl] |
| 74 | 3-Bu—Ph | Ph | Me₃C | 7 | 2-(1,1-dimethylethyl)-1-phenyl-6-(3-butylphenyl) |

TABLE 1-continued

| | Starting Material of Formula II | | | Described in Example | Product: [(prefix listed below)-1,4,5,6-tetrahydropyrimidine] Prefix |
|---|---|---|---|---|---|
| Example | R¹ | R² | R³ | | |
| 75 | 4-Br—Ph | Ph | Me₃C | 7 | 2-(1,1-dimethylethyl)-1-phenyl-6-(4-bromophenyl) |
| 76 | 4-C₅H₁₁—O—Ph | Ph | Me₃C | 7 | 2-(1,1-dimethylethyl)-1-phenyl-6-(4-pentoxyphenyl) |
| 77 | Ph | Ph | 3-pyridinyl | 8 | 1,6-diphenyl-2-(3-pyridinyl), nmr (CDCl₃) δ 2.23(m), 3.70(t), 5.03(t), 7.20(m), 7.42(m), 7.90(t), 8.50(d) and 8.75(d) and HBr salt, mp > 250° C. |
| 78 | Ph | 2-Me—Ph | 3-pyridinyl | 8 | 6-phenyl-1-(2-methylphenyl)-2-(3-pyridinyl) |
| 79 | Ph | 4-(C₅H₁₁)—Ph | 3-pyridinyl | 8 | 6-phenyl-1-(4-pentylphenyl)-2-(3-pyridinyl) |
| 80 | Ph | 3-Cl—Ph | 3-pyridinyl | 8 | 6-phenyl-1-(3-chlorophenyl)-2-(3-pyridinyl) |
| 81 | Ph | 4-I—Ph | 3-pyridinyl | 8 | 6-phenyl-1-(4-iodophenyl)-2-(3-pyridinyl) |
| 82 | Ph | 2-EtO—Ph | 3-pyridinyl | 8 | 6-phenyl-1-(2-ethoxyphenyl)-2-(3-pyridinyl) |
| 83 | Ph | 3-Me₂CH—Ph | 3-pyridinyl | 8 | 6-phenyl-1-[3-(1-methylethyl)phenyl]-2-(3-pyridinyl) |
| 84 | 3-Bu—Ph | Ph | 3-pyridinyl | 8 | 1-phenyl-6-(3-butylphenyl)-2-(3-pyridinyl) |
| 85 | 4-Br—Ph | Ph | 3-pyridinyl | 8 | 1-phenyl-6-(4-bromophenyl)-2-(3-pyridinyl) |
| 86 | 4-C₅H₁₁—O—Ph | Ph | 3-pyridinyl | 8 | 1-phenyl-6-(4-pentoxyphenyl)-2-(3-pyridinyl) |

EXAMPLE 87

2-(4-Morpholinylmethyl)-1,6-diphenyl-1,4,5,6-tetrahydropyrimidine (I; R¹ and R²=C₆H₅ and R³=4-morpholinylmethyl)

A solution of 2-chloromethyl-1,6-diphenyl-1,4,5,6-tetrahydropyrimidine (15.0 g, 52.7 mmoles, described in Example 21) in morpholine (60 g) is stirred 18 hr at room temperature. The mixture is filtered and the filtrate is evaporated. The residue is dissolved in methylene chloride and the solution is washed with 10% aqueous potassium carbonate, water, brine, dried over magnesium sulfate and evaporated to give a residue (12.6 g) of the title compound, nmr (CDCl₃) δ 2.0(m), 2.25(t), 2.65(m), 2.90(s), 3.53(t), 4.64(m) and 7.07-7.14(m). The title compound is dissolved in isopropanol and dry hydrogen bromide gas is bubbled into the solution. Diethyl ether is added and the precipitate is collected and crystallized from methanol-diethyl ether to give the hydrobromide salt (7.6 g) of the title compound, mp 228°-229° C.

Anal: Calcd for $C_{21}H_{27}N_3OBr_2$: C, 50.71; H, 5.47; N, 8.45%. Found: C, 50.80; H, 5.38; N, 8.38%.

In the same manner but replacing 2-chloromethyl-1,6-diphenyl-1,4,5,6-tetrahydropyrimidine with an equivalent amount of the title compound described in Example 22, 23, 24, 29 or 31, the following compounds of formula I are obtained, respectively: 2-[2-(4-morpholinyl)ethyl]-1,6-diphenyl-1,4,5,6-tetrahydropyrimidine, 2-[2-(4-morpholinyl)-1,1-dimethylethyl]-1,6-diphenyl-1,4,5,6-tetrahydropyrimidine, 2-[3-(4-morpholinyl)propyl]-1,6-diphenyl-1,4,5,6-tetrahydropyrimidine, 2-(4-morpholinylmethyl)-6-phenyl-1-(2-ethoxyphenyl)-1,4,5,6-tetrahydropyrimidine and 2-(4-morpholinylmethyl)-1-phenyl-6-(3-butylphenyl)-1,4,5,6-tetrahydropyrimidine.

EXAMPLE 88

2-(N,N-Dimethylaminomethyl)-1,6-diphenyl-1,4,5,6-tetrahydropyrimidine (I; R¹ and R²=C₆H₅ and R³=CH₂NMe₂)

A solution of 2-chloromethyl-1,6-diphenyl-1,4,5,6-tetrahydropyrimidine (18.2 g, 64.0 mmoles, described in Example 21) in methanol is added to a solution of dimethylamine in methanol [prepared by addition of dimethylamine hydrochloride (15.7 g, 192 mmoles) to potassium hydroxide (2.8 g) in methanol (200 ml)]. The mixture is stirred 18 hr at room temperature, filtered and evaporated. A portion of residue (1.0 g) is chromatography on alumina (Woelm, basic, activity 111) by increasing the solvent polarity from benzene to chloroform. The appropriate eluates are evaporated to give a residue (0.150 g) of the title compound, nmr (CDCl₃) δ 2.15(s), 2.2(m), 2.92(s), 3.45(m), 4.8(t) and 7.2-7.3(m).

In the same manner but replacing dimethylamine with an equivalent amount of dipropylamine or N-butyl-N-ethylamine, the following compounds of formula I are obtained, respectively: 2-(N,N-dipropylaminomethyl)-1,6-diphenyl-1,4,5,6-tetrahydropyrimidine and 2-(N-butyl-N-ethylaminomethyl)-1,6-diphenyl-1,4,5,6-tetrahydropyrimidine.

We claim:

1. A compound of formula I

(I)

in which R¹ and R² are phenyl and R³ is lower alkyl, phenyl, 2-furyl, 3-pyridinyl, 2-thienyl, di(lower alkyl)amino or a radical of formula R⁴—A wherein A is lower alkylene and R⁴ is 1-piperidinyl or 4-morpholinyl; or a therapeutically acceptable acid addition salt thereof.

2. A compound of formula I

(I)

in which R¹ and R² are phenyl and R³ is lower alkyl, phenyl or di(lower alkyl)amino; or a therapeutically acceptable acid addition salt thereof.

3. A compound of formula I

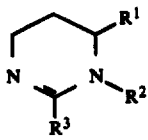 (I)

in which $R^1$ and $R^2$ are phenyl and $R^3$ is 2-furyl, 3-pyridinyl, 2-thienyl or a radical of formula $R^4$—A wherein A is lower alkylene and $R^4$ is 1-piperidinyl or 4-morpholinyl; or a therapeutically acceptable acid addition salt thereof.

4. 1,2,6-Triphenyl-1,4,5,6-tetrahydropyrimidine, as claimed in claim 1.

5. 1,6-Diphenyl-2-(1-piperidenylmethyl)-1,4,5,6-tetrahydropyrimidine, as claimed in claim 3.

6. 2-(1,1-Dimethylethyl)-1,6-diphenyl-1,4,5,6-tetrahydropyrimidine, as claimed in claim 1.

7. 2-Methyl-1,6-diphenyl-1,4,5,6-tetrahydropyrimidine, as claimed in claim 1.

8. 2-(2-Furyl)-1,6-diphenyl-1,4,5,6-tetrahydropyrimidine, as claimed in claim 3.

9. 2-(Thienyl)-1,6-diphenyl-1,4,5,6-tetrahydropyrimidine, as claimed in claim 3.

10. 2-Dimethylamino-1,6-diphenyl-1,4,5,6-tetrahydropyrimidine, as claimed in claim 1.

11. 1,6-Diphenyl-2-(3-pyridinyl)-1,4,5,6-tetrahydropyrimidine, as claimed in claim 3.

12. 2-(4-Morpholinylmethyl)-1,6-diphenyl-1,4,5,6-tetrahydropyrimidine, as claimed in claim 3.

* * * * *